(12) United States Patent
Reimels (10) Patent No.: US 9,788,970 B2
(45) Date of Patent: Oct. 17, 2017

(54) EXPANDABLE INTERBODY SPACER

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 449 days.

(21) Appl. No.: 14/336,918

(22) Filed: Jul. 21, 2014

(65) Prior Publication Data

US 2016/0015529 A1 Jan. 21, 2016
US 2017/0239065 A9 Aug. 24, 2017

Related U.S. Application Data

(63) Continuation of application No. 13/414,876, filed on Mar. 8, 2012, now abandoned.

(60) Provisional application No. 61/466,729, filed on Mar. 23, 2011.

(51) Int. Cl.
*A61F 2/44* (2006.01)
*A61F 2/46* (2006.01)
*A61F 2/30* (2006.01)

(52) U.S. Cl.
CPC ............ *A61F 2/4465* (2013.01); *A61F 2/446* (2013.01); *A61F 2/4611* (2013.01); *A61F 2002/30019* (2013.01); *A61F 2002/3097* (2013.01); *A61F 2002/30224* (2013.01); *A61F 2002/30235* (2013.01); *A61F 2002/30263* (2013.01); *A61F 2002/30545* (2013.01); *A61F 2002/30553* (2013.01); *A61F 2002/30579* (2013.01); *A61F 2002/30774* (2013.01); *A61F 2002/30873* (2013.01); *A61F 2002/4475* (2013.01)

(58) Field of Classification Search
CPC ............ A61F 2/4465; A61F 2002/4475; A61F 2/446; A61F 2/4455; A61F 2002/30224; A61F 2002/30235
See application file for complete search history.

(56) References Cited

U.S. PATENT DOCUMENTS

| 2012/0245691 A1* | 9/2012 | Reimels | A61F 2/446 623/17.16 |
| 2013/0123927 A1* | 5/2013 | Malandain | A61B 17/8852 623/17.16 |

FOREIGN PATENT DOCUMENTS

WO WO2010/103344 * 9/2010 .............. A61F 2/44

* cited by examiner

*Primary Examiner* — Matthew Lawson
(74) *Attorney, Agent, or Firm* — Dinsmore & Shohl LLP (57) ABSTRACT

An expandable intervertebral spacer includes a body, a proximal end, and a distal end. The body includes quadrants that form a substantially cylindrical shape in a first configuration and a substantially cuboidal shape in a second configuration. Each quadrant includes a ramp portion with a ramp and a landing and a sliding portion with a sliding side and a foot. The ramp portion of a first quadrant engages the sliding portion of a second quadrant. The proximal end and the distal end couple with the plurality of quadrants and transfer an actuating force to expand the body from the first configuration to the second configuration.

19 Claims, 5 Drawing Sheets

EXPANDABLE INTERBODY SPACER

CROSS REFERENCE TO RELATED APPLICATIONS

This application is a continuation of U.S. application Ser. No. 13/414,876 filed on Mar. 8, 2012, U.S. application Ser. No. 13/414,876 claims priority to U.S. Provisional Application No. 61/466,729, filed Mar. 23, 2011, and the content of both is incorporated herein by reference in its entirety.

FIELD

The present disclosure generally relates to the field of spinal orthopedics, and more particularly to intervertebral implants and interbody devices.

BACKGROUND

The spine is a flexible column formed of a plurality of bones called vertebrae. The vertebrae are hollow and stacked one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The intervertebral fibro-cartilages are also known as intervertebral discs and are made of a fibrous ring filled with pulpy material. The discs function as spinal shock absorbers and also cooperate with synovial joints to facilitate movement and maintain flexibility of the spine. When one or more discs degenerate through accident or disease, nerves passing near the affected area may be compressed and are consequently irritated. The result may be chronic and/or debilitating back pain. Various methods and apparatus have been designed to relieve such back pain, including spinal fusion using an interbody spacer or suitable graft using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in these techniques, also commonly referred to as interbody spacers, are placed in the inter-discal space between adjacent vertebrae of the spine. Many times an exterior plate is used in conjunction with the interbody spacer to hold the adjacent vertebrae while the fusion occurs.

Ideally, the interbody spacer should stabilize the intervertebral space and allow fusion of the adjacent vertebrae. Moreover, during the time it takes for fusion to occur, the interbody spacer should have sufficient structural integrity to withstand the stress of maintaining the space without substantially degrading or deforming and have sufficient stability to remain securely in place prior to actual bone fusion.

Interbody spacers have been used successfully to fuse adjoining vertebral bodies to restore anatomical positioning and eliminate pain caused by a bulging disc. Spacers fit into the disc space and support the vertebral bodies allowing bone fusion to occur between the joint surfaces. The primary technical advances in this market have been in the methods of minimally invasive interbody delivery. Anterior delivery and more recently medial delivery have reduced morbidity and allowed faster patient rehabilitation.

One major obstacle remaining in perfecting these procedures is reducing the displacement of soft tissue structures and the size of tissue dissections to place the relatively large interbodies necessary to properly support the spinal column during the bone remodeling process. Large interbodies also require extensive site preparation and sizing prior to placement. This site prep can cause increased trauma to surrounding structures as instrumentation is manipulated in the disc space.

SUMMARY

An expandable intervertebral spacer includes a body, a proximal end, and a distal end. The body includes quadrants that form a substantially cylindrical shape in a first configuration and a substantially cuboidal shape in a second configuration. Each quadrant includes a ramp portion with a ramp and a landing and a sliding portion with a sliding side and a foot. The ramp portion of a first quadrant engages the sliding portion of a second quadrant. The proximal end and the distal end couple with the quadrants and transfer an actuating force to expand the body from the first configuration to the second configuration.

In other features, the quadrants are integrally formed within the body. The ramp of the first quadrant engages a sliding side of the second quadrant in the first configuration. The landing of the first quadrant engages a foot of the second quadrant in the second configuration. A plurality of integral linking members couple the proximal and distal ends with the body. A plurality of integral linking members conform to the cylindrical shape in the first configuration and plastically deform when the body transforms to the second configuration. A tension member couples the first quadrant and the second quadrant. A tension member within the body includes a first length in the first configuration and a second length greater than the first length in the second configuration. An integral tension member within the body provides tension between the first quadrant with the second quadrant as the body expands from the first configuration to the second configuration. A threaded aperture is disposed within at least one of the proximal end and the distal end.

An apparatus for expanding an intervertebral space includes a plurality of interlocking sections, a proximal end, and a distal end all integrally formed in a body. The plurality of interlocking sections integrally formed in the body is configurable between a first geometry and a second geometry. The proximal end and the distal end integrally formed in the body are configured to transfer an applied force to configure the body between the first geometry and the second geometry.

In other features, a first of the interlocking sections slidably engages a second of the interlocking sections as the body transforms from the first geometry to the second geometry. The plurality of interlocking sections includes four quadrants that form a cylindrical arrangement in the first geometry and a cuboidal arrangement in the second geometry. At least one of the interlocking sections includes a sliding quadrant and at least one of the interlocking sections includes a ramp quadrant. A sliding side of a first interlocking section slides along a ramp of an adjacent second interlocking section as the applied force compresses the proximal and distal ends. A first of the interlocking sections includes a first sliding quadrant linked to a first ramp quadrant by a first bridge. A tension member integrally formed in the body links two of the interlocking sections. The first geometry fills a first volume and the second geometry fills a second volume greater than the first volume. One of the proximal and distal ends includes an attachment feature and the other of the proximal and distal ends includes an anti-rotation feature. A tension member linking two of the interlocking sections plastically deforms when the interlocking sections transform from the first configuration to the second configuration.

DETAILED DESCRIPTION

The use of a smaller interbody which may be expanded in-situ allows the possibility of performing the surgery percutaneously with minimal disruption to tissues surrounding the surgical site and intervening soft tissue structures. The expandable interbody spacer of the present disclosure includes features that reduce displacement of soft tissue and structures during placement of the interbody while providing support to the vertebrae while bone fusion occurs. The spacer includes a first configuration that may be a substantially cylindrical geometry with dimensions that allow percutaneous insertion of the spacer between the vertebrae. Once the spacer is positioned in a desired location between the vertebrae, the spacer may be expanded to a second configuration. The second configuration may be a substantially cuboidal geometry with dimensions that allow the spacer to fill the disc space and provide support to the adjacent vertebrae while bone fusion occurs. The second configuration provides rigid support between the adjacent vertebrae that withstands compressive forces.

The expandable interbody spacer includes a system and method of expanding a compact cylindrical form into a cuboidal shaped implant which has the necessary structural integrity to support the load of the spinal column during bone remodeling and fusion. This design uses positive cam action of sections or quadrants as they slide pass one another to expand the implant. The use of cam action allows the precise control of the rate of expansion and ensures each segment deploys evenly.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

Referring now to FIGS. 1-8, an expandable interbody spacer 100 of the present disclosure includes a system of sections or quadrants and linking members that expand from a substantially cylindrical shape in a first configuration to a substantially cuboidal shape in a second configuration. The quadrants may be substantially rigid in construction and the linking members may be semi-rigid, flexible, and/or plastically deformable. The spacer 100 may include a substantially cylindrical shape to enable insertion through a circular, percutaneous surgical opening in a patient. For example, the spacer 100 may include a proximal end 102 having a circular profile, a cylindrical body 104, and a distal end 106 also having a circular profile. The body 104 may be segmented into the system of quadrants and linking members as described herein. The quadrants and linking members may be formed in the body 104 from a unitary construction. That is, the quadrants and linking members may be integral and continuous with the body 104. For example, the quadrants and linking members may be cut using laser cutting techniques or other methods in order to retain a unitary construction. In other examples, the quadrants and linking members may be joined together by other methods.

Figure 1:
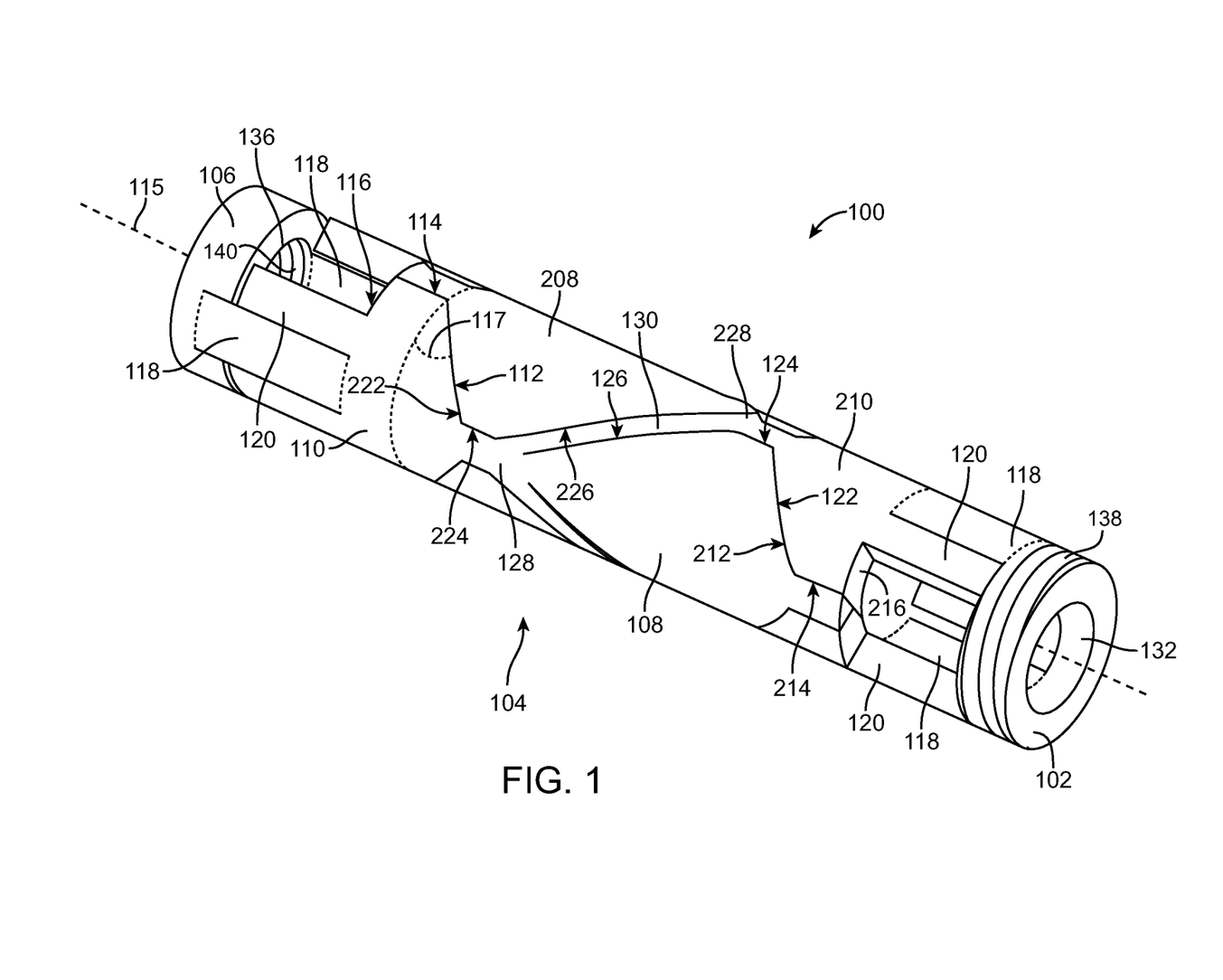
FIG. 1 is a perspective view of an expandable interbody spacer in a first configuration according to the principles of the present disclosure.

FIG. 1 illustrates the spacer 100 in the first configuration prior to percutaneous insertion into the patient. The body 104 of the spacer 100 may be described with reference to multiple sections or quadrants, each of which includes similar subsections or components. For example, a first quadrant of the body 104 includes a first sliding portion 108 coupled with a first ramp portion 110 that together extend the length of the body 104. The first sliding portion 108 and the first ramp portion 110 include curved outer surfaces corresponding to the overall cylindrical shape of the spacer 100 when in the first configuration. The first ramp portion 110 includes a ramp 112, a landing 114, and a compressive side 116. The first ramp portion 110 may include additional sides to form a substantially irregular pentagonal shape. The ramp 112 may include an angle 117 relative to the circumference of the body 104. The landing 114 extends from the ramp 112 and substantially parallel to a longitudinal axis 115 of the body 104. The compressive side 116 extends from the landing 116 substantially parallel to the circumference of the body 104. A compressive linking member 118 may flexibly couple the compressive side 116 to the distal end 106 of the spacer 100. Various tabs 120 may also extend from the compressive side 116 and towards the distal end 106.

The first sliding portion 108 includes a sliding side 122, a foot 124, and a central side 126. The first sliding portion 108 may include additional sides that may also form a substantially irregular pentagonal or hexagonal shape. The sliding side 122 includes the same angle 117 relative to the circumference of the body 104 and is substantially parallel to the ramp 112. The foot 124 extends from the sliding side 122 substantially parallel to the axis 115 of the body 104.

The central side 126 extends from the foot 124 towards a first bridge 128. The first bridge 128 may link the first sliding quadrant 108 to the first ramp portion 110. The first bridge 128 may be substantially rigid to withstand compressive forces applied to the compressive side 116 of the first ramp portion 110 so as not to buckle between the first sliding portion 108 and the first ramp portion 110. The first bridge 128 may be integral and continuous with the first sliding portion 108 and the first ramp portion 110.

Continuing with FIG. 1, a second quadrant of the body 104 includes a second sliding portion 208 coupled with a second ramp portion 210 that together extend the length of the body 104. The second sliding portion 208 and the second ramp portion 210 include curved outer surfaces corresponding to the overall cylindrical shape of the spacer 100. The second ramp portion 210 includes a ramp 212, a landing 214, and a compressive side 216. The second ramp portion 210 may include additional sides and feet that may form a substantially irregular pentagonal shape. The ramp 212 extends along the surface of the body 104 at a similar angle as the angle 117 relative to the circumference of the body 104. The landing 214 extends from the ramp 212 substantially parallel to the axis 115 of the body 114. The compressive side 216 extends from the landing 214 substantially parallel to the circumference of the body 214. A compressive member 118 couples the compressive side 216 to the proximal end 102 of the spacer 100. Various tabs 120 may also extend from the compressive side 216 and towards the proximal end 102.

The second sliding portion 208 includes a sliding side 222, a foot 224, and a central side 226. The second sliding portion 208 may include additional sides that may also form a substantially irregular pentagonal or hexagonal shape. The sliding side 222 extends along the surface of the body 104 at an angle similar to the angle 117 and substantially parallel to the ramp 112. The sliding side 222 is configured to slide relative to the ramp 112 when the spacer 100 transforms from the first configuration to the second configuration. The foot 224 extends from the sliding side 222 substantially parallel to the longitudinal axis 115 of the body 104. The central side 226 extends from the foot 224 towards a second bridge 228. The second bridge 228 may link the second sliding portion 208 to the second ramp portion 210. The second bridge 228 may be substantially rigid to withstand compressive forces applied to the compressive side 216 of the second ramp portion 210 so as not to buckle between the second sliding portion 208 and the second ramp portion 210. The second bridge 228 may be integral and continuous with the second sliding portion 208 and the second ramp portion 210.

Figure 2:
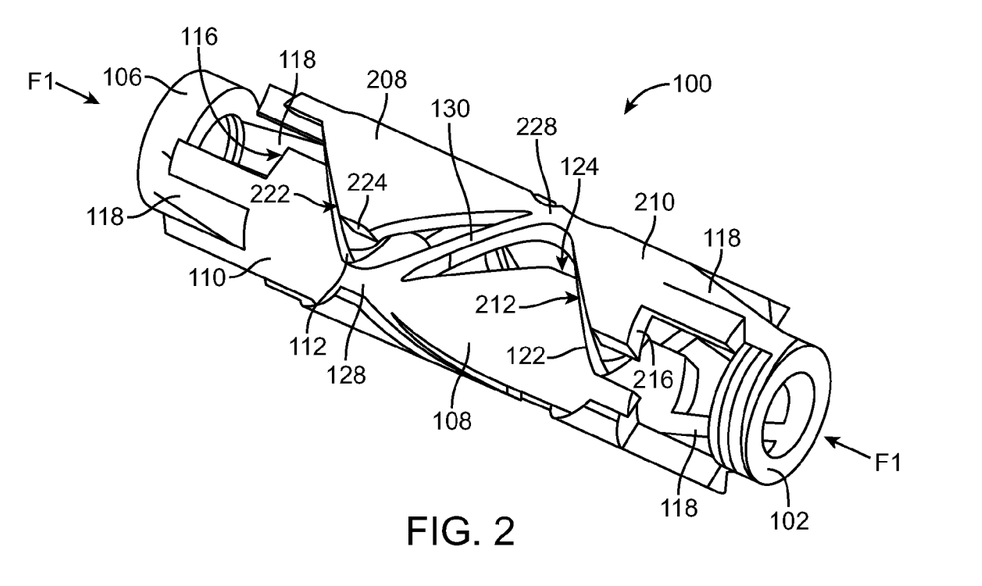
FIG. 2 is a perspective view of the expandable interbody spacer begins to expand from the first configuration to a second configuration according to the principles of the present disclosure.
Figure 3:
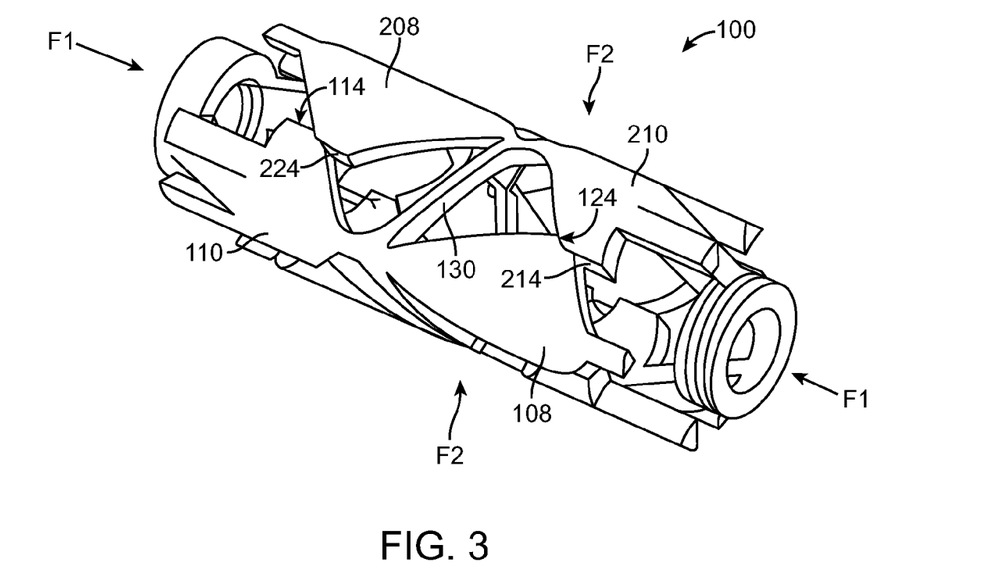
FIG. 3 is a perspective view of the expandable interbody spacer prior to full expansion in the second configuration according to the principles of the present disclosure.
Figure 4:
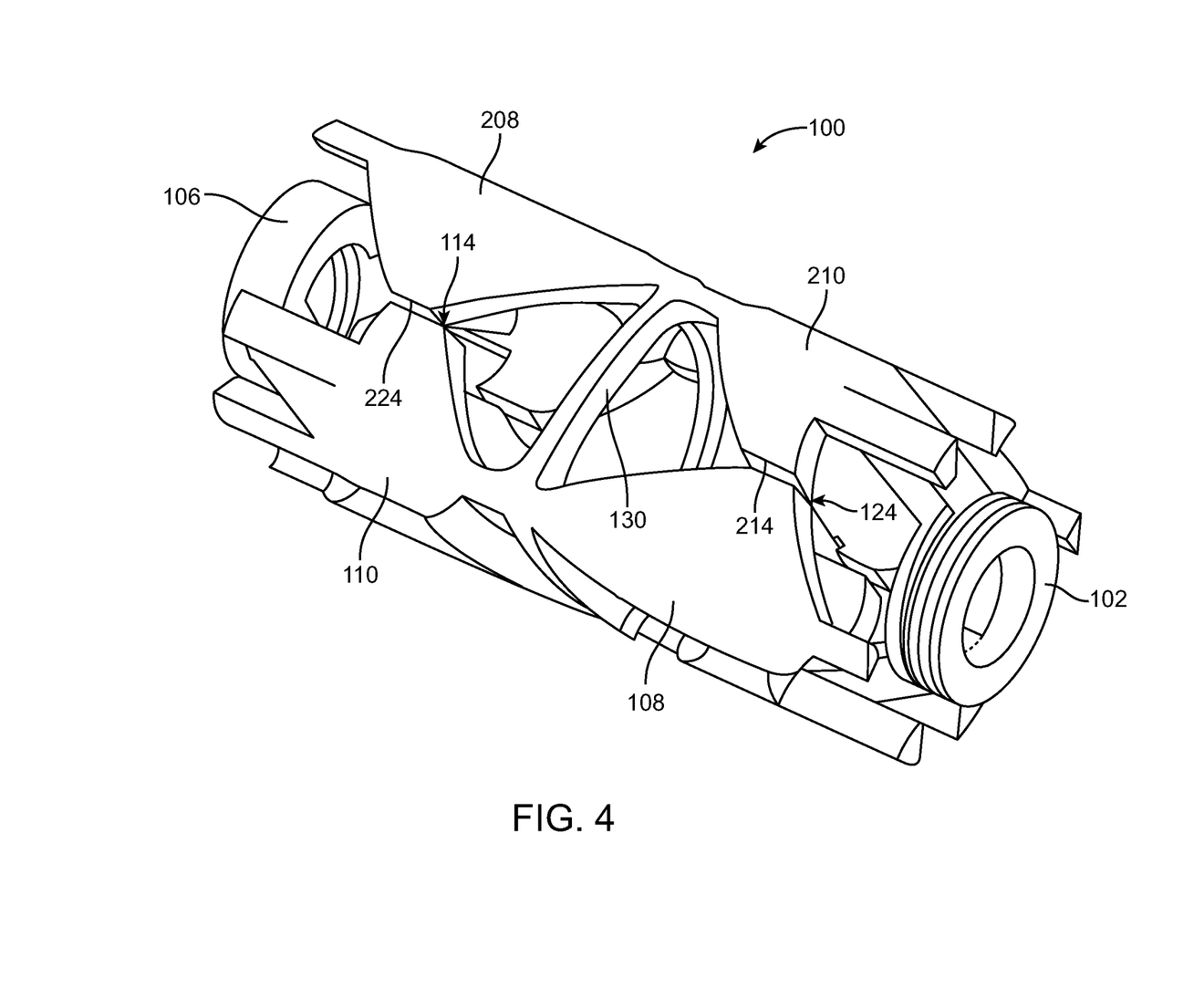
FIG. 4 is a perspective view of the expandable interbody spacer in the second configuration according to the principles of the present disclosure.

A first tension member 130 extends from the first bridge 128 to the second bridge 228 and couples the first quadrant and the second quadrant of the body 104. The tension member 130 may be formed by the central sides 126 and 226 of the first sliding portion 108 and the second sliding portion 208 respectively. The tension member 130 may include flexible or semi-rigid regions that enable the tension member 130 to elastically deflect, stretch, or bend as the spacer 100 transforms from the first configuration to the second configuration as illustrated in FIGS. 2-4. The tension member 130 may provide resistive force or tension that provides an interference fit between the landings and feet as described herein. Once in the second configuration, the tension member 130 may include rigid characteristics to withstand compressive forces associated with placement in the intervertebral disc space in the second configuration. For example, plastic deformation of the tension member 130 may alter the physical characteristics of the constituent material and increase rigidity.

Figure 7:
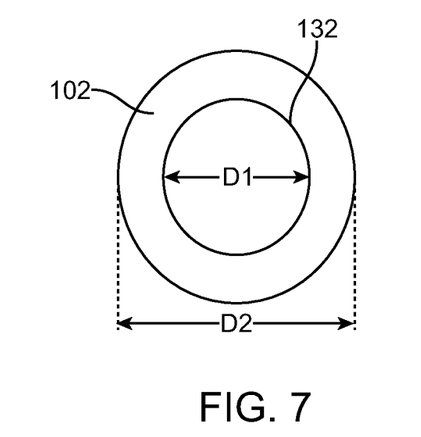
FIG. 7 is an elevational side view of the proximal end of the expandable interbody spacer in the first configuration according to the principles of the present disclosure.
Figure 8:
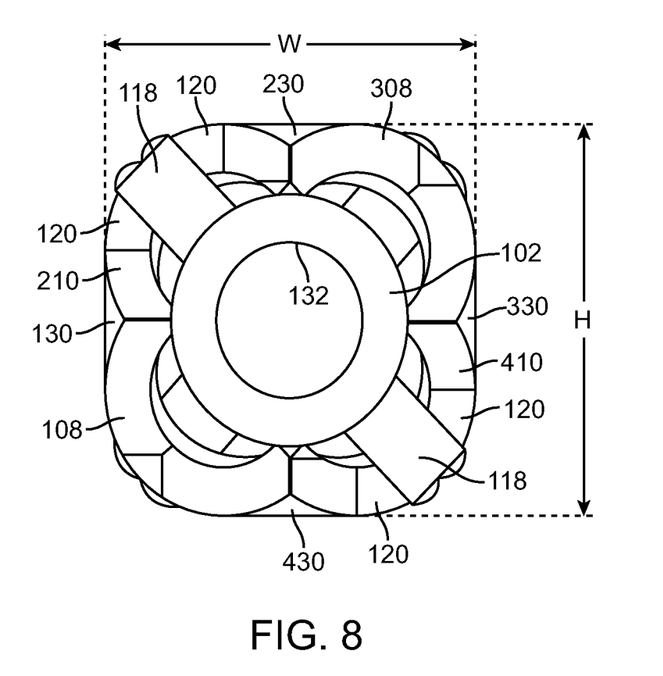
FIG. 8 is an elevational side view of the proximal end of the expandable interbody spacer in the second configuration according to the principles of the present disclosure.

The body 104 may include additional quadrants having sliding portions and ramp portions similar to the first and second quadrants described above, such as a third quadrant and a fourth quadrant, that are substantially identical to and/or mirror images of the first and second quadrants. Each adjacent quadrant is linked by an additional tension member that extends from the bridge of one quadrant to the bridge of another quadrant. In the present example, four quadrants that each includes a sliding portion, a ramp portion, and a bridge may be linked by four tension members to expand from the cylindrical first configuration as illustrated in FIGS. 1 and 7 to form a substantially cuboidal second configuration as illustrated in FIGS. 4 and 8. Generally, the first configuration, such as the cylindrical arrangement, includes a first volume corresponding to the diameter D2 and length of the cylinder. The second configuration, such as the cuboidal arrangement, includes a second volume corresponding to the length of the spacer 100 and an expanded width W and height H. The second volume is greater than the first volume.

For purposes of expediency and clarity, actuation of the spacer 100 will be described with reference to the first and second quadrants only. However, one skilled in the art may appreciate that the same interaction between sliding portions and ramp portions applies to the additional third and fourth quadrants. Furthermore, one skilled in the art may appreciate that any suitable number of sections may be included in the spacer 100 to achieve various geometric configurations.

Referring back to FIG. 1, in the first configuration, the first ramp portion 110 and the second sliding portion 208 are adjacent to one another and the second ramp portion 210 and the first sliding portion 108 are adjacent to one another. The outer surface of the body 104 may be substantially uniform as the sides of all the sections are substantially in alignment. The proximal end 102 of the spacer 100 may include a first aperture 132 for insertion of a deployment tool, such as the exemplary deployment tool provided in U.S. Publication No. 2009/0318928, incorporated herein by reference. The deployment tool may pass through the center of the spacer 100 and exit through the distal end 106 via a second aperture 136. Various attachment features of the deployment tool may couple with the proximal end 102 and or the distal end 106 to enable percutaneous insertion into the patient. For example, threads 138 on the proximal end and threads 140 on the distal end 104 may provide for attachment of the deployment tool. Once the spacer 100 has been inserted and positioned within the intervertebral space between two vertebrae, the deployment tool may actuate to deploy and expand the spacer 100 by applying a compressive force F1 to either or both ends of the spacer 100 as shown in FIGS. 2 and 3.

Continuing now with FIG. 2, as the force F1 acts on the ends 102 and 106 of the spacer 100, each of the compressive members 118 begins to push against the first and second compressive sides 116 and 216 of the first and second ramp portions 110 and 210 respectively. The ramp 112 of the first ramp portion 110 slidably engages with the sliding side 222 of the second sliding portion 208. Likewise, the ramp 212 of the second ramp portion 210 slidably engages with the sliding side 122 of the first sliding portion 108. The compressive force F1 forces the ends 102 and 106 towards each other and the sliding engagement of the sliding portions and ramp portions guides the movement of the first and second sections relative to each other. Thus, the second section begins to move away from the first section causing the spacer 100 to expand. The tension member 130 may begin to elastically bend near the first bridge 128 and the second bridge 228. The foot 224 of the second sliding portion 208 begins to move away from the first bridge 128 and the foot 124 of the first sliding portion 108 begins to move away from the second bridge 228.

Continuing now with FIG. 3, as the foot 124 of the first sliding portion 108 approaches the landing 214 of the second ramp portion 210, the tension member 130 continues to deform. The tension member may provide some counterforce F2 that pulls the first sliding portion 108 and the second ramp portion 210 together. The counterforce F2 may cause some interference between the foot 124 of the first sliding portion 108 and the landing 214 of the second ramp portion 210 as the spacer 100 expands to the second configuration. For example, the tension member 130 may elastically stretch while also resisting the movement of the second ramp portion 210 away from the first sliding portion 108. Similarly, as the foot 224 of the second sliding portion 208 approaches the landing 114 of the first ramp portion 110, the counterforce F2 may pull the second sliding portion 208 and the first ramp portion 110 together. The counterforce F2 may cause some interference between the foot 224 of the second sliding portion 208 and the landing 114 of the first ramp portion 110. For example, the interference between each foot and landing interface may require an increase in the force F1 applied to the proximal end 102 and distal end 106 of the spacer 100 in order to fully deploy the spacer 100. The interference may provide tactile feedback to the surgeon as indication of full deployment.

Referring now to FIG. 4, as the feet 124 and 224 of each sliding portion 108 and 208 clear the landings 114 and 214 of each ramp portion 110 and 210, the first and second sections of the body 104 may be fully expanded in the second configuration. Thus, the feet 124 and 224 and landings 114 and 214 mate to create a stable, 4-sided expanded structure in the second configuration. The alignment of each portion to a corresponding ramp portion provides stability and support to withstand compressive forces associated with inter-vertebral implantation. The supporting members 130 may provide additional support to the spacer 100 in the second configuration.

Figure 5:
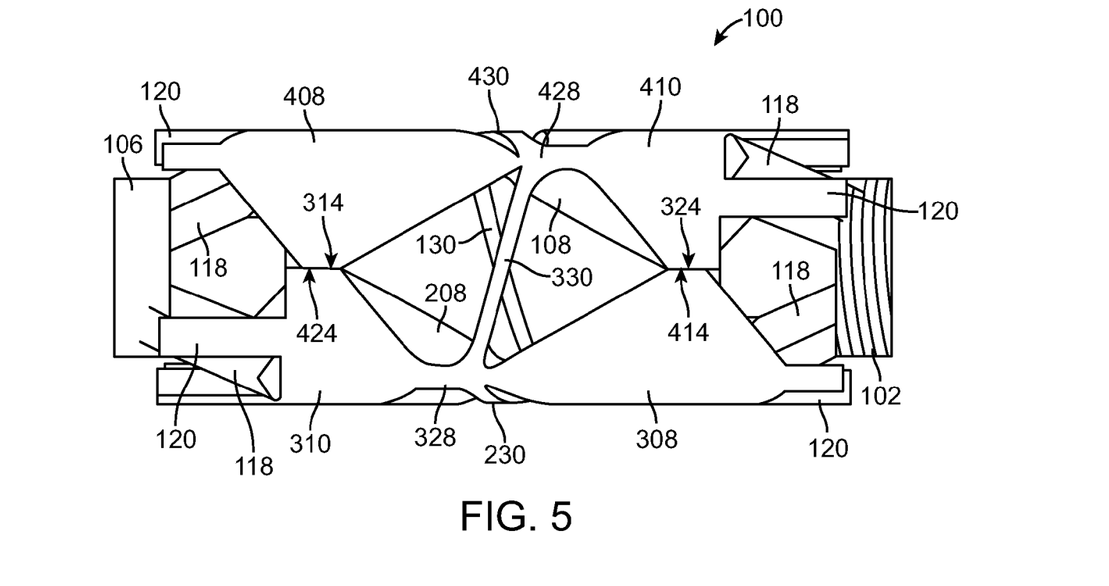
FIG. 5 is an elevational side view of the expandable interbody spacer in the second configuration according to the principles of the present disclosure.
Figure 6:
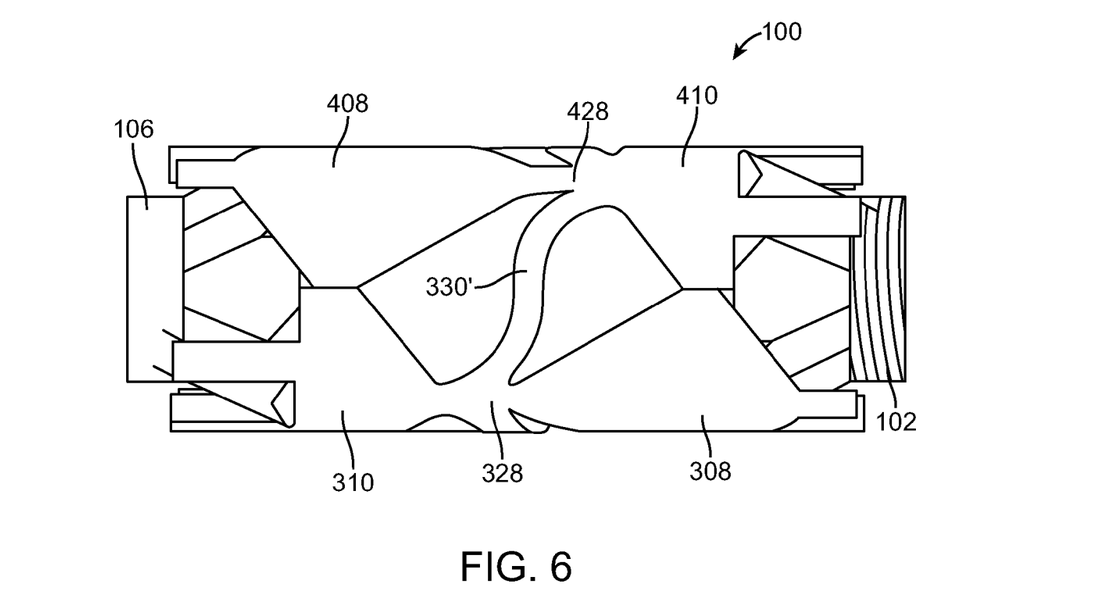
FIG. 6 is an elevational side view of the expandable interbody spacer illustrating deformation of a tension member of the interbody spacer according to the principles of the present disclosure.

Referring now to FIG. 5, a side view of the spacer 100 in the second configuration illustrates additional features of the third and fourth quadrants of the spacer 100. The third section of the spacer 100 includes a third sliding portion 308 coupled with a third ramp portion 310 by a third bridge 328. The fourth section includes a fourth sliding portion 408 coupled with a fourth ramp portion 410 by a fourth bridge 428. A foot 424 of the fourth sliding portion 408 contacts a landing 314 of the third ramp portion 310. A foot 324 of the third sliding portion 308 contacts a landing 414 of the fourth ramp portion 410. Contact between each pair of feet and landings provides rigid support to adjacent vertebrae after deployment within the intervertebral disc space. A tension member 330 links the third bridge 328 with the fourth bridge 428 and may provide additional support. Additional tension members 230 and 430 link the second bridge 228 (not shown) with the third bridge 328 and the fourth bridge 428 with the first bridge 128 (not shown). In FIG. 6, another side view of the spacer in the second configuration illustrates how another tension member 330' may deform during transition from the first configuration to the second configuration. For example, the tension member 330' may flex more than the tension members illustrated in FIGS. 1-5 and begin to resemble an "S" shape.

Referring now to FIGS. 7 and 8, side views looking into the proximal end 102 of the spacer 100 illustrate the cylindrical first configuration and the expanded cuboidal second configuration in greater detail. In FIG. 7, the spacer 100 is shown in the non-deployed first configuration. Thus, the proximal end 102 and the aperture 132 are the only visible features of the spacer 100. The aperture 132 may include an inner diameter D1. The inner diameter D1 may be configured for attachment of the deployment tool or other suitable device. The spacer 100 may include an outer diameter D2 prior to deployment that is suitable for percutaneous insertion into the patient. Once the spacer 100 has been inserted into the intervertebral disc space, the deployment tool (not shown) or other suitable device may be used to apply the force F1 as illustrated in FIGS. 2 and 3. In FIG. 8, the spacer 100 expands to the deployed second configuration, and the sliding portions 108 and 308 and ramp portions 210 and 410 thus radially expand away from the axial center of the spacer 100. Once the sliding portions 108 and 308 and ramp portions 210 and 410 reach the second configuration, the spacer 100 may include a width W and a height H that are greater than the outer diameter D2 of the spacer 100.

In operation, the spacer 100 may be inserted into the intervertebral disc space between two vertebrae using a deployment tool. An exemplary deployment tool may be found in commonly assigned U.S. Pub. No. 2010/0228301, entitled "Attachment Device and Methods of Use," to Greenhalgh et al. which is incorporated herein by reference. In some cases, the disc space may include a degenerated disc or other disorder that may require a partial or complete discectomy prior to insertion of the spacer 100. The deployment tool may engage with the proximal end 102 and the distal end 106 of the spacer 100. For example, the deployment tool may engage with the threads 138 and 140 on at least one of the proximal end 102 and the distal end 106 respectively. At one end, such as the distal end 106, the deployment tool may prevent rotation of the spacer 100. At the other end, such as the proximal end 102, the deployment tool may engage the thread 138 to pull the proximal end 102 and distal end 106 together. As the deployment instrument applies the force F1, the spacer 100 gradually expands as described above. The deployment instrument may increase the amount of force F1 as interference between each foot and landing resists expansion of the spacer 100. The increase in the force F1 may provide tactile feedback to the surgeon indicating near complete deployment of the spacer 100. As each foot snaps onto its respective landing, the force F1 may decrease quickly providing additional feedback that the spacer 100 is fully deployed and structurally rigid.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. An intervertebral spacer for placement between adjacent vertebrae, comprising: a body, the body being plastically deformable and of unitary construction, the body having a generally tubular shape bounding an open space, the body including a plurality of slits so as to define a first section having a first edge, a second section having a second edge and a tension member, the body including a length with a longitudinal axis, expandable radially from the longitudinal axis from a first height to a larger second height by plastic deformation of the body, and the first section including a foot, the second section including a landing, the tension member connecting the first section to the second section, the foot and the landing not engaged with each other at the first height and configured to directly engage each other at the second height to form a rigid body, wherein the first edge slides against the second edge when the body is longitudinally compressed so as to radially expand the body.

2. The intervertebral spacer of claim 1, wherein the first section further includes a ramp and the second section further includes a sliding side, the ramp and the sliding side engaged with each other at the first height and not engaged with each other at the second height.

3. The intervertebral spacer of claim 2, wherein the ramp and the sliding side slide relative to one another as the body expands from the first height to the second height.

4. The intervertebral spacer of claim 1, wherein the tension member is configured to apply tension to provide interference between the foot and the landing as the body expands from the first height to the second height.

5. The intervertebral spacer of claim 1, wherein the body forms a cylindrical geometry at the first height and a cuboidal geometry at the second height.

6. The intervertebral spacer of claim 1, wherein the unitary construction includes a monolithic body of an integrally formed plurality of sections.

7. The intervertebral spacer of claim 1, further comprising a proximal end and a distal end of the body configured to receive a compressive force to plastically deform the body.

8. The intervertebral spacer of claim 1, further comprising one or more threaded apertures formed in the body and configured to couple with a deployment tool.

9. The intervertebral spacer of claim 1, further comprising an attachment feature on a proximal end of the body and an anti-rotation feature on a distal end of the body.

10. An expandable intervertebral spacer, comprising: a body being plastically deformable and of a unitary construction having a proximal end, a distal end, and a plurality of slits defining a plurality of sections between the proximal end and distal end, wherein the plurality of sections have an edge, the body having a generally tubular shape bounding an open space, the body including a first length, a first width, and a first height in a first configuration and a second length less than the first length, a second width greater than the first width, and a second height greater than the first height in a second configuration; a first of the sections including a ramp portion with a ramp and a landing; and a second of the sections including a sliding portion with a sliding side and a foot; wherein the proximal end and the distal end are configured to receive a compressive force that causes the edge of the plurality of sections to slide against each other so as to radially expand the body member, and wherein the longitudinal compressive force further urges the ramp to slide along the sliding side as the body expands from the first configuration to the second configuration, and wherein the foot does not engage the landing in the first configuration and engages the landing in the second configuration to form a structurally rigid body.

11. The expandable intervertebral spacer of claim 10, wherein the first configuration includes a cylindrical profile with the first width substantially the same as and the first height.

12. The expandable intervertebral spacer of claim 10, further comprising an attachment feature on the proximal end configured to attach to a deployment tool and an aperture in the proximal end configured to receive a portion of the deployment tool therethrough.

13. The expandable intervertebral spacer of claim 10, further comprising an aperture in the distal end configured to attach to a portion of a deployment tool.

14. The expandable intervertebral spacer of claim 10, further comprising a tension member dividing the first of the sections from the second of the sections in the first configuration and applying a tensile force resisting expansion of the body to the second configuration.

15. An expandable intervertebral spacer, comprising: a body being plastically deformable and of a unitary construction having a proximal end, a distal end, and a plurality slits defining a plurality of sections between the proximal end and distal end, and forming a cylindrical geometry bounding an open space, the body having a first length and a first height corresponding to a radius of the cylindrical geometry in an unexpanded configuration and a cuboidal geometry in an expanded configuration with a second length less than the first length, a second width greater than the radius, and a second height greater than the radius.

16. The expandable intervertebral spacer of claim 15, wherein a first of the sections includes a ramp portion with a ramp and a landing and a second of the sections including a sliding portion with a sliding side and a foot.

17. The expandable intervertebral spacer of claim 16, wherein the proximal end and the distal end are configured to receive a compressive force that causes the ramp to slide along the sliding side as the body expands from the first configuration to the second configuration.

18. The expandable intervertebral spacer of claim 16, wherein the foot does not engage the landing in the first configuration.

19. The expandable intervertebral spacer of claim 16, wherein the foot engages the landing in the second configuration to form a structurally rigid body.

* * * * *